United States Patent
Perregaard

[11] Patent Number: 5,972,964
[45] Date of Patent: Oct. 26, 1999

[54] AMINOMETHYLINDANS, -BENZOFURANS AND -BENZOTHIOPHENES

[75] Inventor: Jens Perregaard, Jægerspris, Denmark

[73] Assignee: H. Lundbeck A/S, Copenhagen-Valby, Denmark

[21] Appl. No.: 08/955,376

[22] Filed: Oct. 22, 1997

Related U.S. Application Data

[62] Division of application No. 08/504,847, Jun. 6, 1995, Pat. No. 5,807,889, which is a continuation of application No. PCT/DK93/00413, Dec. 8, 1993.

[30] Foreign Application Priority Data

Dec. 9, 1992 [DK] Denmark ................ 1482/92

[51] Int. Cl.⁶ ............... A61K 31/445; C07D 405/12
[52] U.S. Cl. ............... 514/324; 514/200; 514/212; 514/320; 514/401; 514/402; 514/408; 514/422; 514/443; 514/456; 514/595; 514/659; 540/596; 540/609; 546/196; 546/202; 546/205; 548/316.4; 548/525; 548/579; 548/950; 548/962; 548/967; 549/49; 549/462; 564/52; 564/928
[58] Field of Search ............... 514/200, 212, 514/320, 324, 401, 402, 408, 422, 443, 456, 595, 659; 540/596, 609; 546/196, 202, 205; 548/316.4, 525, 579, 950, 962, 967; 549/49, 462; 564/57, 428

[56] References Cited

U.S. PATENT DOCUMENTS

| | | | |
|---|---|---|---|
| 3,980,658 | 9/1976 | Possanza et al. | 546/201 |
| 4,500,543 | 2/1985 | Debernardis et al. | 514/469 |
| 4,530,932 | 7/1985 | Clemence et al. | 514/318 |
| 4,670,447 | 6/1987 | Strupczewski | 514/322 |
| 4,847,254 | 7/1989 | Boegesoe et al. | 514/256 |
| 4,861,789 | 8/1989 | Berge | 514/370 |
| 4,946,863 | 8/1990 | Boegesoe et al. | 514/447 |
| 5,130,334 | 7/1992 | Arrowsmith | 514/469 |
| 5,196,454 | 3/1993 | Grauert | 514/654 |
| 5,225,596 | 7/1993 | Carlsson | 564/428 |
| 5,561,152 | 10/1996 | Freeman | 514/466 |

FOREIGN PATENT DOCUMENTS

| | | | |
|---|---|---|---|
| 0 357 415 A2 | 3/1990 | European Pat. Off. | A61K 31/00 |
| 0 402 923 A2 | 6/1990 | European Pat. Off. | C07C 211/60 |
| 2 391 211 | 4/1976 | France | C07D 405/14 |
| 28 27 874 | 6/1978 | Germany | C07D 401/08 |
| 3 924 365 A1 | 1/1991 | Germany | C07C 237/48 |
| 2 093 837 | 9/1982 | United Kingdom | C07C 9/28 |
| WO 87/00043 | 1/1987 | WIPO | A61K 9/00 |
| WO 89/06645 | 7/1989 | WIPO | C07C 91/28 |
| W O92/00070 | 1/1992 | WIPO | A61K 31/445 |

OTHER PUBLICATIONS

Ahlennis, *Pharm. Tox.*, 64:3 (1989).
Cerro et al., *Eur. J. Pharm.*, 158:53 (1988).
DeBernardis et al., *J. Med. Chem.*, 28:1398 (1985).
Gillis et al., *J. Pharm. Exp. Ther.*, 248:851 (1989).
Glitz, D. A.. et al., *Drugs*, 41:11 (1991).
Hicks, *Life Science*, 47:1609 (1990).
Hyttel et al., *J. Neurolchem.*, 44:1615 (1985).
Lowe et al., *J. Med. Chem.*, 34:1860 (1991).
Martin et al., *J. Med. Chem.*, 32:1052 (1991).
Pedersen et al., *Acta Pharmacol. Toxicol.*, 31:488–96 (1972).
Prehn, *Eur. J. Pharm.*, 203:213 (1991).
Saxena et al., *Pharmacology of Antihypertensive Therapeuties, Handb. Exp. Pharm.*, 93 Springer Verlag, pp. 533–558 (1990).
Saxena et al., *Trends Pharm. Sci. II*, 95 (1990).
Sanchez, C. et al., *Drug Dev. Res.*, 22:239–50 (1991).
Schipper, *Human Psychopharm.*, 6:S53 (1991).
Tonoue, T. et al., *Psychoneuro–endocrinology*, 11:177–84 (1986).
Tricklebank, M.D. et al., *Euro. J. Pharmacol*, 133:47–56 (1987).
Van Hest, *Psychopharm*, 107:474 (1992).
Wadenberg et al., (1991), *J. Neural Transm.*, 83:43.
DeBernardis et al., *J. Med. Chem.*, 28:1398:1404 (1985).
Perregaard et al., CA 124:232261) (1995).

*Primary Examiner*—Ceila Chang
*Attorney, Agent, or Firm*—Darby & Darby

[57] ABSTRACT

Compounds of formula I

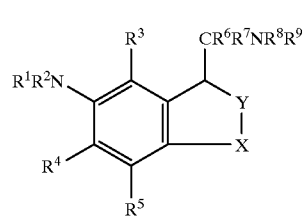

wherein R1=(cyclo)alk(en)yl, aralkyl, alkyl(oxy)carbonyl, CONH2, etc.; R2=H, (cyclo)alk(en)yl, aralkyl, etc.; R3–R5=H, halo, alkyl, alkoxy, etc.; R6,R7=H, alkyl; R6R7=atoms to complete a ring; R8,R9=groups cited for R2, 2-oxoimidazolidinoalkyl, etc.; NR8R9=heterocyclyl; 1 of X,Y=CH2 and the other=CH2, O, S were prepd. Thus, 1-indancarboxylic acid was converted in 5 steps to 1-(N,N-dipropylaminomethyl)-6-formylaminoindane oxalate which had ED50 of 0.0055.mu.M/kg s.c. in the 8—OH DPAT cue agonism test in rats.

14 Claims, No Drawings

5,972,964

AMINOMETHYLINDANS, -BENZOFURANS AND -BENZOTHIOPHENES

This is a division, of application Ser. No. 08/504,847, filed Jun. 6, 1995, now U.S. Pat. No. 5,807,889, which is a continuation of PCT/DK93/00413 filed Dec. 8, 1993.

FIELD OF THE INVENTION

The present invention relates to a novel class of substituted aminomethylindans, —2,3-dihydrobenzofuranes, —2,3-dihydrobenzothiophenes, —1,3-dihydroisobenzofuranes, and —1,3-dihydroisobenzothiophenes having effect at central 5-$HT_{1A}$ receptors. These aminomethyl compounds are therefore useful in the treatment of certain psychic and neurologic disorders.

BACKGROUND OF THE INVENTION

A few aminomethylindans and related compounds are known from the prior art.

So, EP patent 0 281 261 discloses 1-aminomethylindan, 3-aminomthylbenzofurane and 3-aminomthylbenzothiophene derivatives with a hydroxy group or a substituted hydroxy group in the 6-position (indan) or 5-position (benzofurane, benzothiophene). These compounds were found to show central dopamine agonist activity, in particular to show effect at presynaptic dopamine receptors.

GB Patent No. 2 093 837 A relates to a class of 1-aminoalkyl tetraline derivatives having one or more hydroxy or alkoxy substituents in the 5-, 6- and/or 7-position and claimed to show adrenergic and dopaminergic effects, thus being useful in the treatment of hypertension. DeBernardis et al. in J. Med. Chem., 1985, 28 (10), 1398–1404 discuss such effects with respect to dihydroxy-substituted aminomethyltetralines, -indans and benzocyclobutenes.

EP Patent No. 0 402 923 A2 discloses 2,5-diaminotetraline derivatives alleged to have central dopamine agonistic activity, with different compounds interacting with different functional dopamine receptors, thus having different therapeutical effects, such as effects in schizophrenia, hypertension and Parkinsonism.

DE Patent No. 39 24 365 A1 describes a class of 2-amino-7-carbamoyltetraline derivatives said to have presynaptic dopamine agonistic properties, and accordingly antihypertensive and heart rate decreasing effects and effects in the central nervous system.

In U.S. Pat. No. 4,500,543 certain 1-aminomethylphtalane compounds are said to show adrenergic effects and, accordingly, antihypertensive and heart rate decreasing properties. Said patent generically covers compounds having substituents in the 5-, 6- and/or 7-position.

FR Patent No. 2 548 146 relates to 3-aminomethylthiophtalide and 3-aminomethylisobenzofuranethione derivatives claimed to have analgesic and/or anticonvulsive effects.

None of these references discuss or suggest that any of the compounds have 5-$HT_{1A}$ receptor activity.

Clinical studies of known compounds having 5-$HT_{1A}$ agonistic activity, such as buspirone, 8-[4-[4-(2-pyrimidyl)-1-piperazinyl]butyl]-8-azaspiro[4,5]decane-7,9-dione, gepirone, 4,4-dimethyl-1-[4-[4-(2-pyrimidyl)-1-piperazinyl]butyl]-2,6-piperidinedione and ipsapirone, 2-[4-[4-(2-pyrimidyl)-1-piperazinyl]butyl]-1,2-benzothiazol-3 (2H)-one-1,1-dioxide, have shown that such compounds are useful in the treatment of anxiety disorders such as generalised anxiety disorder, panic disorder, and obsessive compulsive disorder (Glitz, D. A., Pohl, R., Drugs 1991, 41, 11). Also preclinical studies indicate that compounds with 5-$HT_{1A}$ agonistic effects are useful in the treatment of the above mentioned anxiety related disorders (Schipper, Human Psychopharm., 1991, 6, S53).

There is also evidence, both clinical and preclinical, in support of the beneficial effect of compounds having 5-$HT_{1A}$ agonistic activity in the treatment of depression as well as impulse control disorders and alcohol abuse (van Hest, Psychopharm., 1992, 107, 474; Schipper et al, Human Psychopharm., 1991, 6, S53; Cervo et al, Eur. J. Pharm., 1988, 158, 53; Glitz, D. A., Pohl, R., Drugs 1991, 41, 11). 5-$HT_{1A}$ agonistsic compounds inhibits isolation-induced aggression in male mice indicating that these compounds are useful in the treatment of aggression (Sanchéz et al, Psychopharmacology, 1992, in press).

Furthermore, compounds having 5-$HT_{1A}$ agonistic activity have been reported to show antipsychotic effect in animal models (Wadenberg and Ahlenius, J. Neural Transm, 1991, 83, 43; Ahlenius, Pharm. Tox., 1989, 64, 3; Lowe et al., J. Med. Chem., 1991, 34, 1860; New et al., J. Med. Chem., 1989, 32, 1147; and Martin et al., J. Med. Chem., 1989, 32, 1052).

Recent studies also indicate that 5-$HT_{1A}$ receptors are important in the serotonergic modulation of haloperidol-induced catalepsy (Hicks, Life Science 1990, 47, 1609) suggesting that 5-$HT_{1A}$ agonists are useful in the treatment of the side effects induced by conventional antipsychotic agents such as e.g. haloperidol.

Compounds having 5-$HT_{1A}$ agonistic activity have shown neuroprotective properties in rodent models of focal and global cerebral ischaemia and may, therefore, be useful in the treatment of ischaemic disease states (Prehn, Eur. J. Pharm. 1991, 203, 213).

Both in animal models and in clinical trials it has been shown that 5-$HT_{1A}$ agonists exert anthihypertensive effects via a central mechanism (Saxena and Villalón, Trends Pharm. Sci. 1990, 11, 95; Gillis et al, J. Pharm. Exp. Ther. 1989, 248, 851). Compounds having 5-$HT_{1A}$ agonistic activity may, therefore, be beneficial in the treatment of cardiovascular disorders.

Accordingly, compounds having 5-$HT_{1A}$ agonistic activity are believed to be useful in the therapy of such conditions, and thus being highly desired.

SUMMARY OF THE INVENTION

It has now been found that certain novel aminomethylindans, -2,3-dihydrobenzofuranes, -2,3-dihydrobenzothiophenes, -1,3-dihydroisobenzofuranes and -1,3-dihydroisobenzothiophenes have agonistic effect at central 5-$HT_{1A}$ receptors.

Accordingly, the present invention relates to a novel class compounds having general Formula I:

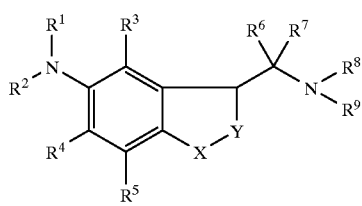

wherein one of X and Y is CH$_2$ and the other one is selected from the group consisting of CH$_2$, O and S;

R$^1$ is selected from the group consisting of lower alkyl, lower alkenyl, lower alkynyl, cycloalk(en)yl, cycloalk(en)yl-lower alk(en/yn)yl, aryl-lower alkyl, acyl, lower-alkyl sulphonyl, trifluoromethylsulfonyl, arylsulphonyl, R$^{10}$ZCO— where Z is O or S and R$^{10}$ is alkyl, alkenyl, alkynyl, cycloalk(en)yl, cycloalk(en)ylalkyl, or aryl, or R$^{11}$R$^{12}$NCO— where R$^{11}$ and R$^{12}$ are independently hydrogen, alkyl, alkenyl, alkynyl, cycloalk(en)yl, cycloalk(en)ylalk(en/yn)yl, or aryl;

R$^2$ is selected from the group consisting of hydrogen, lower alkyl, lower alkenyl, lower alkynyl, cycloalk(en)yl, cycloalk(en)yl-lower alk(en/yn)yl, aryl-lower alkyl;

R$^3$–R$^5$ are independently selected from the group consisting of hydrogen, halogen, lower alkyl, lower alkoxy, acyl, lower alkylthio, hydroxy, lower alkylsulphonyl, cyano, trifluoromethyl, cycloalkyl, cycloalkylalkyl or nitro;

R$^6$ and R$^7$ are each hydrogen or lower alkyl or they are linked together to constitute a 3–7-membered carbocyclic ring;

R$^8$ and R$^9$ are independently hydrogen, alkyl, alkenyl, alkynyl, cycloalk(en)yl, cycloalk(en)yl-alk(en/yn)yl, arylalkyl or a group

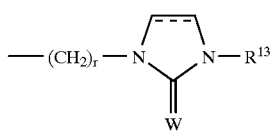

wherein R$^{13}$ is hydrogen, lower alkyl, lower alkenyl, lower alkynyl, cycloalk(en)yl, cycloalk(en)yl-lower alk(en/yn)yl, aryl-lower alkyl or aryl, W is O or S, and r is 2–6; or R$^8$ and R$^9$ are linked together in order to form a 3–7 membered ring containing one nitrogen atom;

any alkyl, cycloalkyl or cycloalkylalkyl group present being optionally substituted with one or two hydroxy groups, which again are optionally esterified with an aliphatic or aromatic carboxylic acid; and any aryl substituent present being optionally substituted with halogen, lower alkyl, lower alkoxy, lower alkylthio, hydroxy, lower alkylsulfonyl, cyano, trifluoromethyl, cycloalkyl, cycloalkylalkyl or nitro;

and pharmaceutically acceptable acid addition salts thereof.

In general the compounds of the invention have been found potently to inhibit the binding of tritiated 8-hydroxy-2-dipropylaminotetralin (8-OH-DPAT) to 5-HT$_{1A}$ receptors in vitro. Furthermore, the present compounds have in general proven to show 5-HT$_{1A}$ agonistic properties in vivo and they have been found to show effects in animal models predictive of antipsychotic and anxiolytic properties, respectively. Accordingly, the compounds of the invention are considered useful as drugs for the treatment of psychosis, anxiety disorders, such as generalised anxiety disorder, panic disorder, and obsessive compulsive disorder, depression, impulse control disorders, alcohol abuse, aggression, ischaemic diseases, side effects induced by conventional antipsychotic agents or cardiovascular disorders.

Accordingly, in another aspect the invention provides a pharmaceutical composition comprising at least one novel compound according to the invention as defined above or a pharmaceutically acceptable acid addition salt thereof thereof in a therapeutically effective amount and in combination with one or more pharmaceutically acceptable carriers or diluents.

In a further aspect the present invention provides the use of a compound according to the invention or a pharmaceutically acceptable acid addition salt thereof for the manufacture of a pharmaceutical preparation for the treatment of psychosis, anxiety disorders, depression, impulse control disorders, alcohol abuse, aggression, ischaemic diseases, side effects induced by conventional antipsychotic agents or cardiovascular disorders.

DETAILED DESCRIPTION OF THE INVENTION

Some of the compounds of general Formula I may exist as optical isomers thereof and such optical isomers are also embraced by the invention.

As used herein the term alkyl refers to a C$_1$–C$_{20}$ straight chain or branched alkyl group and similarly alkenyl and alkynyl mean a C$_2$–C$_{20}$ straight chain or branched hydrocarbon group having one or more double bonds or tripple bonds, respectively. The term cycloalkyl designates a carbocyclic ring having 3–8 carbon atoms, inclusive, or a bicyclic or tricyclic carbocycle, such as adamantyl.

The terms lower alkyl, lower alkoxy, lower alkylthio, etc. refer to such branched or unbranched groups having from one to six carbon atoms inclusive. Exemplary of such groups are methyl, ethyl, 1-propyl, 2-propyl, 1-butyl, 2-butyl, 2-methyl-2-propyl, 2-methyl-1-propyl, methoxy, ethoxy, 1-propoxy, methylthio, ethylthio, 1-propylthio, 2-propylthio, methylsulfonyl, ethylsulfonyl, or the like. Similarly lower alkenyl and lower alkynyl refer to such groups having from two to six carbon atoms, inclusive, and one or more double or tripple bonds, respectively.

The expression alk(en/yn)yl means that the group may be an alkyl, alkenyl or alkynyl group.

The term aryl refers to a mono- or bicyclic carbocyclic or heterocyclic aromatic groups, such as phenyl, indolyl, thienyl, furanyl, pyridyl, thiazolyl, benzofuranyl, benzothienyl, benzisothiazolyl and benzisoxazolyl.

Halogen means fluoro, chloro, bromo or iodo.

As used herein the term acyl refers to a formyl, alkylcarbonyl, alkenylcarbonyl, alkynylcarbonyl, arylcarbonyl, arylalk(en/yn)ylcarbonyl, cycloalkylcarbonyl or cycloalkylalk(en/yn)ylcarbonyl group.

In Formula I, X is preferably CH$_2$, O or S and Y is CH$_2$.

R$^1$ is preferably an aryl-lower alkyl group, an acyl group, a lower alkylsulfonyl group or a group R$^{11}$R$^{12}$N—CO— wherein R$^{11}$ is hydrogen or lower alkyl and R$^{12}$ is hydrogen, alkyl, aryl, or cycloalkyl. Most preferably, R$^1$ is benzyl or substituted benzyl, formyl, alkylcarbonyl, in particular acetyl, arylcarbonyl, in particular benzoyl or substituted benzoyl, or a group $R^{11}R^{12}N-CO-$ wherein $R^{11}$ is hydrogen or lower alkyl and $R^{12}$ is hydrogen, lower alkyl, phenyl, substituted phenyl, or $C_{5-6}$ cycloalkyl.

$R^2$ is preferably hydrogen or lower alkyl, each of $R^3$, $R^4$, $R^5$ is preferably hydrogen or halogen and $R^6$ and $R^7$ are preferably both hydrogen.

$R^8$ is preferably hydrogen or lower alkyl, and preferably $R^9$ is lower alkyl, aryl-lower alkyl, cycloalkyl-lower alkyl or a group of Formula 1a, wherein W is O and $R^{13}$ is hydrogen, lower alkyl, cycloalkyl or aryl, or alternatively $R^8$ and $R^9$ are connected in order to form a $C_3$–$C_7$ membered ring containing one nitrogen atom. Most preferably $R^9$ is phenyl-lower alkyl, substituted phenyl-lower alkyl, indolyl-lower alkyl, cyclohexyl-lower alkyl or a group of Formula 1a, wherein W is O and $R^{13}$ is hydrogen or a lower alkyl, cycloalkyl, phenyl or substituted phenyl group, or $R^8$ and $R^9$ are connected in order to form a pyrrolidine or piperidine ring.

The acid addition salts of the invention are pharmaceutically acceptable salts of the compounds of Formula I formed with non-toxic acids. Exemplary of such organic salts are those with maleic, fumaric, benzoic, ascorbic, embonic, succinic, oxalic, bis-methylenesalicyclic, methanesulfonic, ethanedisulfonic, acetic, propionic, tartaric, salicyclic, citric, gluconic, lactic, malic, mandelic, cinnamic, citraconic, aspartic, stearic, palmitic, itaconic, glycolic, p-aminobenzoic, glutamic, benzenesulfonic, and theophyline acetic acids, as well as the 8-halotheophylines, for example 8-bromotheophyline. Exemplary of such inorganic salts are those with hydrochloric, hydrobromic, sulfuric, sulfamic, phosphoric, and nitric acids.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions methods well known in the art may be used, and any pharmaceutically acceptable carriers, diluents, exipients, or other additive usually used in the art may be used.

Conveniently, the compounds of the invention are administered in unit dosage form containing said compounds in an amount of about 0.01 to 50 mg.

The total daily dose usually ranges of about 0.05–500 mg, and most preferably about 0.1 to 20 mg of the active compound of the invention.

The invention moreover relates to a method for the preparation of the novel aminomethyl derivatives of indans, 2,3-dihydrobenzofuranes, 2,3-dihydrobenzothiophenes, 1,3-dihydroisobenzofuranes and 1,3-dihydroisobenzothiophenes of Formula I, comprising:

a) acylating an amino derivative of the following Formula II:

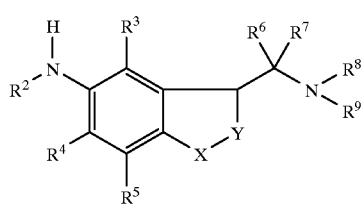

II wherein $R^2$–$R^9$, X, and Y are as previously defined, with an acylating agent such as a carboxylic acid halogenide $R^{1'}CO-hal$, $R^{1'}CO$ being an acyl group embraced by the definition of $R^1$ and hal being halogen, a carboxylic acid anhydride or mixed acid anhydride $R^{1'}CO-OCOR$, R being alkyl, aryl or alkoxy, an isocyanate, isothiocyanate, or a similar activated acylating derivative well-known in the art;

b) in order to prepare a compound of Formula I wherein $R^1$ is lower alkyl, lower alkenyl, lower alkynyl, cycloalk(en)yl, cycloalk(en)yl-lower alk(en/yn)yl or aryl-lower alkyl, alkylating an amino derivative of Formula II with an alkylating agent such as an alkylhalogenide $R^{1''}-hal$, a mesylate $R^{1''}OSO_2CH_3$, a tosylate $R^{1''}OSO_2C_6H_4-CH_3$, or a similar alkylating reagent with suitable leaving groups, $R^{1''}$ being lower alkyl, lower alkenyl, lower alkynyl, cycloalk(en)yl, cycloalk(en)yl-lower alk(en/yn)yl, or aryl-lower alkyl;

c) reducing the double bond in a compound of the following Formula III:

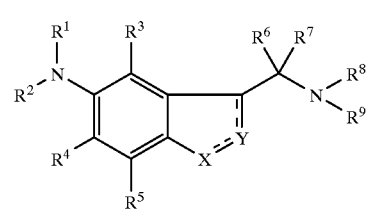

III wherein $R^1$–$R^9$, X, and Y are as previously defined, at least one of X and Y is $CH_2$ and one of the two dotted lines indicates a double bond; or d) alkylating an amine derivative of the following Formula IV:

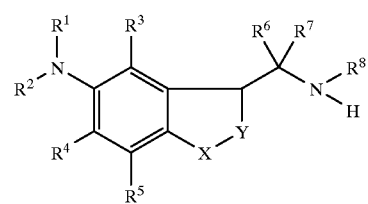

IV wherein $R^1$–$R^8$, X, and Y are as previously defined with an alkylating agent such as an alkylhalogenide $R^9-hal$, a mesylate $R^9OSO_2CH_3$, a tosylate $R^9OSO_2C_6H_4-CH_3$, or similar alkylating reagents with suitable leaving groups, wherein $R^9$ is as previously defined; or e) in order to prepare a compound of Formula I wherein $R^1$ is a group as defined previously, however having a methylene group in the 1-position to the amino group, reducing an amide derivative of the following Formula V:

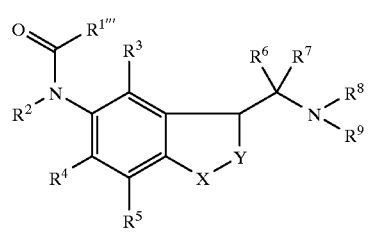

V wherein $R^2$–$R^9$, X and Y are as previously defined and the group $R^{1'''}CH_2$ constitute a group $R^1$; or f) introducing a substituent $R^3$, $R^4$ or $R^5$ by reacting a compound of the following Formula VI:

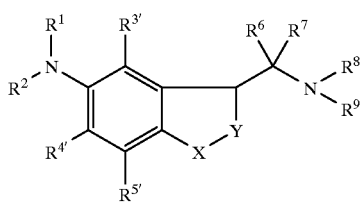

VI wherein at least one of $R^{3'}$–$R^{5'}$ is hydrogen and the others are as previously defined for $R^3$, $R^4$ or $R^5$, and $R^6$–$R^9$, X and Y are as previously defined, by using a reactive reagent such as a halogen or a halogenating agent, sulphonating agent, nitration agent, a reactive agent generating carbonium ions (RCO+, R+) wherein R is alkyl, alkenyl, alkynyl, aryl, cycloalkyl or cycloal(en/yn)yl.

The acylations in Method a) are conveniently performed at low temperatures (eg. below room temperature) in inert solvents such as acetone, dichloromethane, tetrahydrofurane or dimethoxyethane when reactive carboxylic acid chlorides, isocyanates, or isothiocyanates are used. Formylated amines are prepared from the corresponding amines by reaction in formic acid, with esters of formic acid, or by reaction with mixed formic acid anhydride prepared in situ. Generally reaction temperatures are between 0° C. and the boiling point of the formyl precursor compounds.

Alkylations according to Method b) and d) are generally performed by refluxing in a suitable solvent such as acetone, methyl isobutyl ketone, tetrahydrofuran, dioxane, ethanol or 2-propanol in the presence of a base such as triethylamine or potassium carbonate.

Reductions of double bonds according to method c) are generally performed with catalytic hydrogenation at low pressure (<3 atm.) in a Parr apparatus.

The reductions of the amides according to method e) are generally performed by use of $LiAlH_4$, $AlH_3$ or diborane in an inert solvent, such as diethylether, tetrahydrofuran or dioxane at room temperature or at a slightly elevated temperature. Halogenations according to method f) are generally performed by use of chlorine or bromine or N-chlorosuccinamide, N-bromosuccinimid or another halogen precursor molecule, conveniently in the presence of a catalyst such as Fe ions or a mineral acid.

In the following the invention is further illustrated by some examples which, however, may not be construed as limiting.

EXAMPLE 1

1-(N,N-dipropylaminomethyl)-6-formylaminoindan, oxalate 1a (method a)

The starting material, 1-indancarboxylic acid, was prepared according to the procedures of V. Asham and W. H. Linnell, cf. *J. Chem. Soc.* 1954, 4691–4693. A mixture of indancarboxylic acid (32.2 g), thionylchloride (50 ml) and two drops of DMF in dichloromethane (100 ml) was refluxed for 3 hours. Volatile material was evaporated and the remaining crude carboxylic acid chloride was used without further purification. To a solution of N,N-dipropylamine (50 ml) in dichloromethane kept at 0–5° C. was added dropwise a solution of all the crude carboxylic acid chloride in dichloromethane (200 ml). The temperature was gradually raised to room temperature and the reaction mixture was further stirred over-night. The solvents were evaporated in vacuo and the remaining viscous oil was purified by filtering through silica gel (eluted with diethyl ether and dichloromethane 1:1). Yield of N,N-dipropyl-1-indancarboxamide: 32 g. To a well stirred solution of the indancarboxxamide (20 g) in concentrated $H_2SO_4$ (120 ml) kept at −10° C. was added dropwise a cooled mixture of 100% $HNO_3$ (6 g) and concentrated $H_2SO_4$ (40 ml) at −15 to −10° C. The temperature was allowed to raise to 5° C. (not higher to avoid formation of the dinitro compound) and the mixture was subsequently poured onto crushed ice (2 kg). Organic material was extracted with diethyl ether (2×200 ml), the combined organic phase was washed with diluted aqueous $Na_2CO_3$ solution (3×50 ml). The organic phase was dried (anh. $MgSO_4$) and treated with activated carbon. Evaporation of diethyl ether in vacuo afforded N,N-dipropyl-6-nitro-1-indancarboxamide as an oil (15 g). All of this oil was dissolved in 90% ethanol (250 ml). The solution was heated to reflux and Fe powder (10×2 g) and 6 M aqueous HCl (10×0.2 ml) were added portionwise during 1 hour under vigorous stirring. The mixture was refluxed for another hour. Inorganic material was filterted off while the mixture was still hot. The solution was treated with activated carbon and the solvents subsequently evaporated in vacuo. The remaining solid material was recrystallized from a 1:1 mixture of diethyl ether and isopropyl ether yielding 9.5 g of 6-amino-N,N-dipropyl-1-indancarboxamide. Mp: 100° C. To a suspension of $LiAlH_4$ (4 g) in dry THF was added dropwise a solution of all of the 6-aminoindancarboxamide. The mixture was refluxed for 2 hours and subsequently ice-cooled. A mixture of $H_2O$/THF was added cautiously to destroy excess of $LiAlH_4$. Inorganic salts were filtered off and the filter cake was carefully washed with dichloromethane. The solvents were evaporated in vacuo. The remaining oil was dissolved in toluene and excess $H_2O$ was removed by evaporation of toluene leaving the 6-amino-1-(N,N-dipropylaminomethyl)indan as an oil. Yield 7.0 g. To formic acid (98%, 18 ml) was added 3.1 ml of acetic acid anhydride at a temperature just above 0° C. All of the 6-amino-1-(N,N-dipropylaminomethyl)indan was dissolved in dichloromethane (15 ml) and added dropwise at 0–5° C. After 1 h stirring at 5° C. ethyl acetate (100 ml) and dil. aqueous $NH_4OH$ (100 ml) were added. The organic phase was separated and worked-up as above leaving the title compound 1a as an oil. The oxalate salt crystallized from acetone. Yield 7.4 g. Mp: 150–152° C.

In a corresponding way the following N,N-disubstituted 6-formylamino-1-aminomethylindans were prepared:
1-(N,N-dimethylaminomethyl)-6-formylaminoindan, oxalate 1b. Mp: 163–164° C.
6-Formylamino-1-(1-piperidinomethyl)indan, fumarat 1c, Mp: 188–190° C.
6-Formylamino-1-(1-pyrrolidinomethyl)indan, oxalate 1d. Mp: 176–179° C.

EXAMPLE 2

6-Acetylamino-1-(N,N-dipropylaminomethyl)indan, hydrochloride 2a (method a)

To a solution of 6-amino-1-(N,N-dipropylaminomethyl) indan (9 g), prepared as in Example 1, in dichloromethane (50 ml) was added triethylamine (4.2 g). A solution of acetylchloride (3.3 g) in dichloromethane (10 ml) was added dropwise at 0–10° C. The mixture was further stirred at room temperature for ½ hour and finally poured into diluted aqueous $NH_4OH$ (100 ml). The organic phase was separated and worked up yielding 11.0 g of crude title product 2a as an oil. The hydrochloride salt crystallized from acetone. Yield: 9.4 g, mp: 212–216° C.

In a corresponding way the following N,N-disubstituted 6-acylamino-1-aminomethylindans were prepared:

6-Acetylamino-1-(N,N-dimethylaminomethyl)indan, hydrochloride 2b, Mp: 236–238° C.

1-(N,N-dipropylaminomethyl)-6-(4-fluorobenzoylamino) indan, hydrochloride 2c, Mp: 2217–220° C.

6-Acetylamino-7-chloro-1-(N,N-dipropylaminomethyl) indan, oxalate 2f, Mp: 77–79° C. (contains 20% of 6-amino-7-chloro-1-(N,N-dipropylaminomethyl)indan, dioxalate)

1-(N,N-dipropylaminomethyl)-6-(methylsulphonylamino) indan, oxalate 2g, Mp: >300° C.

7-chloro-1-(N,N-dipropylaminomethyl)-6-(methylsulphonylamino)indan, oxalate 2h, Mp: 80–84° C.

5-acetylamino-3-(1-piperidinomethyl)-2,3-dihydrobenzothiophene 2l, Mp: 126–128° C.

EXAMPLE 3

1-(N,N-dipropylaminomethyl)-6-ureido-indan 3a (method a)

To a solution of 6-amino-1-(N,N-dipropylaminomethyl) indan (5 g), prepared as in Example 1, in methanol (10 ml) was added acetic acid (7.3 g). A solution of KOCN (3.3 g) in water (5 ml) was added dropwise at 0–10° C. The mixture was further stirred at room temperture over night. Water (200 ml) and ethylacetate (50 ml) were added and the organic phase was separated and worked up. The fumarate salt of the title compound 3a crystallized from ethanol. The free base was isolated as a crystalline product from the fumarate. Yield 1.1 g. Mp: 101° C.

EXAMPLE 4

1-(N,N-dipropylaminomethyl)-6-(3-phenyl-1-ureido) indan 4a (method a)

To a solution of 6-amino-1-(N,N-dipropylaminomethyl) indan (4.9 g), prepared as in Example 1, in dichloromethane (100 ml) was added phenylisocyanat (3 g). The mixture was refluxed for 1.5 hours. During reaction the title compound 4a crystallized. The mixture was cooled by ice and the precipitated product was filtered off. Yield 4.0 g, mp: 198–201° C.

In a corresponding way were prepared the following N,N-disubstituted 6-ureido-1-aminomethylindans:

1-(N,N-dipropylaminomethyl)-6-(3-methyl-1-ureido)indan, hydrochloride 4b, Mp: 180–182° C.

6-(3,3-dimethyl-1-ureido)-1-(N,N-dipropylaminomethyl) indan, hydrochloride 4c, Mp: 185–187° C.

1-(N,N-dipropylaminomethyl)-6-(3-nonyl-1-ureido)indan, hydrochloride 4d, Mp: 148–150° C. 6-(3-cyclopentyl-1-ureido)-1-(N,N-dipropylaminomethyl)indan, 4e, Mp: 136–138° C.

EXAMPLE 5

3-(N,N-dipropylaminomethyl)-5-formylamino-2,3-dihydrobenzothiophene, oxalate 5a (method a)

The starting material, 5-amino-2,3-dihydro-N,N-dipropyl-3-benzothiophenecarboxamide, was prepared according to the methods in EP Pat. No. 88-301073 CA110 (9):75302y (1988), J. Amer. Chem. Soc. 1948, 70, 1955 and J. Chem. Soc.(c) 1967, 1899. To a solution of the carboxamide (10 g) in THF (200 ml) was added LiAlH₄ pellets (3×1 g) and the mixture was gently refluxed for 2 h. Excess LiAlH₄ was destroyed by cautiously adding a 10% solution of water in THF (25 ml) at 20° C. Inorganic salts were filtered off and the solvents were evaporated in vacuo. The remaining oil (7.0 g) was used without further purification. To the thus obtained crude 5-amino-3-(N,N-dipropylaminomethyl)-2,3-dihydrobenzothiophene in toluene (50 ml), 98% formic acid (20 ml) was added. Toluene/formic acid was gradually destilled off until the temperture reached 130–140° C. Then the mixture was poured onto diluted aqueous NH₄OH (250 ml) and ethyl acetate (100 ml) was added. The organic phase was separated and worked up. The title compound 5a was purified by column chromatography on silica gel (eluted with 3% triethylamine in a 1:1 mixture of dichloromethane and ethyl acetate). A crystalline oxalate salt was obtained from a 15% solution of ethanol in acetone. Yield: 2.4 g. Mp: 135–136° C.

In a corresponding way the following N,N-disubstituted 3-aminomethyl-2,3-dihydrobenzothiophene was prepared:

3-[N-(2-phenylethyl)-N-propylaminomethyl]-5-formylaminomethyl-2,3-dihydrobenzothiophene 5b, isolated as an oil 6-acetylamino-1-(1-piperidinomethyl)indan, oxalate 5c, Mp: 158–160° C.

EXAMPLE 6

1-(N,N-dipropylaminomethyl)-6-(4-fluorobenzylamino)indan, oxalate 6a (method e)

To a solution of 6-amino-N,N-dipropyl-1-indancarboxamide (10 g), prepared as in Example 1, and triethylamine (4.2 g) in dichloromethane (75 ml) kept at −5° C. was added dropwise a solution of 4-fluorobenzoylchloride (6 g) in dichloromethane (30 ml). The temperature was slowly raised to room temperature. Water (200 ml) was added and the organic phase was worked up leaving 15 g of the crude 4-fluorobenzoylamino derivative as an oil. A small sample was purified and crystallized. Mp: 135° C. To a suspension of LiAlH₄ (1 g) in dry THF (50 ml) was added the purified 4-fluorobenzoylamine derivative (3 g) and the mixture was gently refluxed for 1 hour. After cooling, excess LiAlH₄ was destroyed by cautiously adding a 10% solution of water in THF (15 ml) at 20° C. Inorganic salts were filtered off, the filter cake was thouroughly washed with dichloromethane (2×50 ml), and the solvents evaporated leaving the crude title compound 6a as an oil. The oxalate salt (1.5 mol oxalic acid/mol title compound) crystallized from acetone. Yield 1.1 g, mp: 135–140° C.

EXAMPLE 7

5-acetylamino-3-(1-piperidinomethyl)-2,3-dihydrobenzofuran, oxalate 7a (method a)

3-Benzofurancarboxylic acid:

To a solution of benzofuran (75 g) in chloroform (600 ml) was added dropwise a solution of bromine (41 ml) in chloroform (150 ml) at −10° C. The temperature was slowly allowed to reach room temperature and chloroform was evaporated in vacuo, leaving the crude 2,3-dibromo-2,3-dihydrobenzofuran as a crystalline produce which was used without further purification. Yield: 171 g. To the dibromo-derivative (147 g) in ethanol (600 ml) was added a solution of KOH (59 g) in ethanol (200 ml). The mixture was refluxed for 2.5 hours. After cooling to room temperature the mixture was poured onto water and extracted with ethyl acetate (2×300 ml). The combined organic phases were worked-up and the 3-bromobenzofuran was subsequently purified by elution through silica gel using n-heptane as the eluent. Yield 51 g of a semicrystalline product. A solution of all of the thus obtained 3-bromobenzofuran and CuCN (33 g) in N-methyl-2-pyrrolidinone (350 ml) was heated at 190° C. under $N_2$. With 1 hour intervals was added further CuCN (3×4.5 g). The mixture was poured into a solution of $FeCl_3.6H_2O$ in water (610 ml) and concentrated hydrochloric acid (156 ml) while still hot. The resulting mixture was stirred at 60° C. for 1 hour and subsequently poured onto ice/water (5 l). Extraction with diethyl ether (3×300 ml) and working-up of the combined organic phases afforded crude, crystalline 3-cyanobenzofuran melting at 76–82° C. Yield: 34 g. The 3-cyanobenzofuran was dissolved in a mixture of acetic acid:conc. $H_2SO_4$:water 1:1:1 (660 ml) and refluxed for 3 hours. After cooling water was added and the 3-benzofurancarboxylic acid was finally extracted with diethyl ether (3×200 ml) and worked-up. Yield: 37 g. Mp: 152–156° C.

3(1-Piperidylcarbonyl)benzofuran:

A mixture of 3-benzourancarboxylic acid (15 g), N,N-dimethylformamide (2 ml), and thionyl chloride (25 ml) in dichloromethane (200 ml) was refluxed for 5 hours. Volatile material was evaporated in vacuo and excess thionyl chloride was removed by evaporation twice with toluene. The thus obtained 3-benzofurancarboxylic acid chloride was dissolved in dichloromethane (100 ml) and added dropwise to a solution of piperidine (21.4 g) in methylenechloride (100 ml) at 0–5° C. The mixture was further stirred at room temperature for 1 hour. After washing with water and brine, respectively, the organic phase was worked-up as above. The crude piperidino derivative was further purified by column chromatography on silica gel (eluted with a mixture of ethyl acetate/heptane 3:1) yielding 6.7 g of the pure title compound as an oil.

3-(1-Piperidylcarbonyl)-2,3-dihydrobenzofuran:

To a solution of 3-(1-piperidylcarbonyl)benzofuran (6.7 g) in methanol (150 ml) kept at 35–50° C. were added small portions (in total 3 g) of Mg turnings during 5 hours. After stirring for another hour at 50° C. the mixture was poured onto an aqueous solution of $NH_4Cl$. The aqueous solution was extracted with dichloromethane (2×200 ml). The combined organic phases were worked-up yielding 6.7 g of the title 2,3-dihydrobenzofuran derivative as an oil.

5-Nitro-3-(1-piperidylcarbonyl)-2,3-dihydrobenzofuran:

All of the 2,3-dihydrobenzofuran derivative from above was dissolved in trifluoroacetic acid (35 ml) and cooled to 10° C. 65% aqueous $HNO_3$ 4.3 ml was added dropwise below 10° C. The solution which had turned black was immediately poured onto ice and extracted with ethyl acetate (2×50 ml). The combined organic phases were washed thoroughly with an aqueous $Na_2CO_3$ solution (2×25 ml) and finally with brine. Work-up of the organic phase afforded 6.4 g of crude 5-nitro derivative as an oil. Further purification by column chromatography on silica gel (eluted with ethyl acetate/heptane 3:1) yielded 3.2 g of pure 5-nitro-3-(1-piperidylcarbonyl)-2,3-dihydrobenzofuran which crystallized upon standing. Mp: 108–114° C.

5-Amino-3-(1-piperidylcarbonyl)-2,3-dihydrobenzofuran:

To a solution of all of the 5-nitrobenzofuran in 90% ethanol (50 ml) kept at reflux were added small portions of Fe powder (in total 2.5 g) and concentrated HCl (in total 0.1 ml) during 10 min. The mixture was refluxed for another hour. The inorganic precipitates were filtered off and the mixture was poured onto brine and ethyl acetate (250 ml). Work-up of the organic phase afforded 1 g of crystalline 5-aminobenzofuran derivative.

5-Acetylamino-3-(1-piperidinomethyl)-2,3-dihydrobenzofuran, oxalate 7a:

The 5-aminobenzofuran derivative (1 g) dissolved in dry tetrahydrofuran (THF) was added dropwise to a solution of $LiAlH_4$ (0.5 g) in dry THF (30 ml): The mixture was refluxed for 2 hours. After cooling on an ice bath excess $LiAlH_4$ was hydrolyzed by addition of aqueous NaOH solution (0.5 ml 15%). Inorganic salts were filtered off. The THF was evaporated in vacuo and the remaining visceous oil was dissolved in dichloromethane (100 ml). After drying (anh. $MgSO_4$) the dichloromethane was evaporated leaving 0.7 g of crude 5-amino-3-(1-piperidinomethyl)-2,3-dihydrobenzofuran, which was used without further purification. The 5-amino group was acetylated according to the method in EXAMPLE 2. The title compound 7a crystallized as the oxalate salt from acetone. Yield 0.15 g. Mp: 144–150° C.

EXAMPLE 8

Resolution of Compounds (−)-6-Acetylamino-1-(N,N-dipropylaminomethyl) indan, hydrochloride 8a To a solution of 6-Acetylamino-1-(N,N-dipropylaminomethyl)indan (36.5 g) prepared as in Example 2, in acetone was added (S)-(+)-binaphthyl-2,2'-diyl hydrogen phosphate ((+)-BNP) (21.2 g) at reflux. The mixture was cooled and left overnight in a refrigerator. The precipitaated crystalline product was filtered off and the solution was used for the preparation of the other enantiomer 8b. Recrystallization from a 2:3 mixture of methanol and ethanol afforded 30 g of the (+)-BNP salt. Mp: 257–260° C. $[\alpha]_D$=+293.1°. The free base of the title compound 8a was isolated ($[\alpha]$=−84.9°) and subsequently crystallized as the hydrochloride salt from acetone. Mp: 236–238° C., $[\alpha]_D$=−51.3°.

(+)-6-Acetylamino-1-(N,N-dipropylaminomethyl) indan, hydrochloride 8b

The acetone solution from above was poured into water (300 ml) and made alkaline by addition of aqueous diluted NaOH. Extraction with ethyl acetate (2×150 ml) and subsequent crystallization of the (−)-BNP salt from acetone/methanol (1:1). Yield: 24.0 g, mp: 257–260° C., $[\alpha]_D$=−296.9°. The free base was isolated as above ($[\alpha]_D$=+84.9°) and subsequently converted into the hydrochloride salt. Yield. 10.3 g, mp: 236–238° C., $[\alpha]_D$=+54.3°.

Compound 2b was resolved in a corresponding way using O,O-ditoluyltartaric acid as the resolving agent:
(−)-6-Acetylamino-1-(N,N-dimethylaminomethyl)indan, isolated as an oil 8c
(+)-6-Acetylamino-1-(N,N-dimethylaminomethyl)indan, isolated as an oil, 8d Compound 2i was resolved in a corresponding way using O,O-ditoluyltartaric acid as the resolving agent:
(−)-6-acetylamino-1-(1-piperidinomethyl)indan, (+)-O,O-di (4-toluyl)-D-tartrate 8e, Mp: 144–147° C. $[\alpha]_D$=+59.2 (The free base was isolated as above ($[\alpha]_D$=−46.8°)
(+)-6-acetylamino-1-(1-piperidinomethyl)indan, (−)-O,O-di (4-toluyl)-L-tartrate 8f, Mp: 141–146° C. $[\alpha]_D$=−56.3° (The free base was isolated as above ($[\alpha]_D$=+50.7°)

EXAMPLE 9

(−)- and (+)-6-Amino-1-(N,N-dipropylaminomethyl)indan 9a and 9b

Compounds 8a and 8b were hydrolyzed to the corresponding stereoisomers of the 6-aminoindans, respectively:

A solution of (−)-6-Acetylamino-1-(N,N-dipropylaminomethyl)indan (8.4 g) in 10% conc. hydrochloric acid in methanol (100 ml) was refluxed for 8 hours. The solvents were evaporated and the remaining oil was added to diluted aqueous NH$_4$OH (pH>9) and extracted with ethyl acetate (2×100 ml). The organic phase was worked up leaving the (−)-compound 9a as an oil. Yield: 6.5 g, [α]$_D$=−81.3°.

In a corresponding way from 8b was prepared:
(+)-6-Amino-1-(N,N-dipropylaminomethyl)indan 9b, [α]$_D$=+81.4°.

In a similar way compounds 8c, 8d, 9e and 8f were hydrolyzed to:
(−)-6-Amino-1-(N,N-dimethylaminomethyl)indan 9c, isolated as an oil
(+)-6-Amino-1-(N,N-dimethylaminomethyl)indan 9d, isolated as an oil
(−)-6-amino-1-(1-piperidinomethyl)indan 9e, isolated as an oil
(+)-6-amino-1-(1-piperidinomethyl)indan 9f, isolated as an oil

EXAMPLE 10

The following resolved derivatives were prepared from compounds 9a–9f using standard acylation procedures as described above:
(−)-1-(N,N-dipropylaminomethyl)-6-formylaminoindan, oxalate 10a, mp: 149–151° C., [α]$_D$=−44.0°.
(+)-1-(N,N-dipropylaminomethyl)-6-formylaminoindan, oxalate 10b, mp: 152–154° C., [α]$_D$=+43.9°.
(−)-6-(3,3-dimethyl-1-ureido)-1-(N,N-dipropylaminomethyl)indan, hydrochloride 10c, mp: 180–182° C., [α]$_D$=−49.2°.
(+)-6-(3,3-dimethyl-1-ureido)-1-(N,N-dipropylaminomethyl)indan, hydrochloride 10d, mp: 180–182° C., [α]$_D$=+48.8°.
(−)-6-[3-(4-fluorophenyl)-1-ureido]-1-(N,N-dipropylaminomethyl)indan, 10e, mp: 200° C., [α]$_D$=−68.5°.
(+)-6-[3-(4-fluorophenyl)-1-ureido]-1-(N,N-dipropylaminomethyl)indan, 10f, mp: 200° C., [α]$_D$=+69.8°.
(−)-1-(N,N-dimethylaminomethyl)-6-formylaminoindan, oxalate 10g, mp: 167–175° C., [α]$_D$=−57.4°.
(+)-1-(N,N-dimethylaminomethyl)-6-formylaminoindan, oxalate 10h, mp: 161–171° C., [α]$_D$=+59.5°.
(−)-6-formylamino-1-(1-piperidinomethyl)indan, oxalate 10l, Mp: 153–160° C. [α]$_D$=−47.3°.
(+)-6-Formylamino-1-(1-piperidinomethyl)indan, oxalate 10j, Mp: 161–164° C. [α]$_D$=+47.4°.

EXAMPLE 11

(i) 6-Acetylamino-5-chloro-1-(N,N-dipropylaminomethyl)indan, oxalate 11a (method f)

To a solution of 6-acetylamino-1-(N,N-dipropylaminomethyl)indan 2a (3.0 g) in acetic acid (15 ml) was addded SO$_2$Cl$_2$ (1.5 g) in one portion. The temperature raised to 65° C. After stirring at room temperature for 2 hours the mixture was poured into diluted aqueous NH$_4$OH and extracted with diethyl ether (2×50 ml). The combined organic phases were worked up and the title compound 11a was purified by column chromatography on silica gel (eluted with ethyl acetate/heptane/triethylamine 40: 60:3). The oxalic acid salt crystallized from acetone. Yield: 1.3 g, mp: 172–174° C.

The enantiomers of 11a were prepared from the acetyl derivatives 8a and 8b, respectively, by chlorination as described above:
(−)-6-Acetylamino-5-chloro-1-(N,N-dipropylaminomethyl) indan, oxalate 11b, Mp: 188–194° C., [α]$_D$=−35.4°.
(+)-6-Acetylamino-5-chloro-1-(N,N-dipropylaminomethyl) indan, oxalate 11c, Mp: 190–195° C., [α]$_D$=+39.7°.

(ii) 6-Acetylamino-5-bromo-1-(N,N-dipropylaminomethyl)indan, oxalate 11d

To a solution of 6-acetylamino-1-(N,N-dipropylaminomethyl)indan 2a (5.0 g) in acetic acid (50 ml) was added dropwise a solution of Br$_2$ (1.2 ml) in acetic acid at 50–55° C. The mixture was stirred at room temperature overnight. The mixture was poured into water/ethyl acetate, the organic phase was separated and washed with Na$_2$S$_2$O$_3$ (1% aqueous solution). After working up of the organic phase, the remaining oil contained a rather high proportion of unreacted starting material and the title compound was isolated from the mixture by column chromatography on silica gel (eluted with ethyl acetate/heptane/triethylamine 40:60:3). The oxalic acid salt of the title compound 11d crystallized from acetone. Yield: 2.0 g, mp: 156–159° C.

EXAMPLE 12

6-Acetylamino-1-(N-methylaminomethyl)indan, fumarate 12a (method g)

To a solution of 6-acetylamino-1-(N,N-dimethylaminomethyl)indan 2b (54 g) in dioxane (1 L) a solution of 2,2,2-trichloroethyl chloroformate (48.7 g) in dioxane (200 ml) was added dropwise at 50° C. The mixture was subsequently kept at 50–60° C. for 0.5 h. The solvent was evaporated and the carbamate was purified by filtering through silica (eluted with ethyl acetate). Yield of the crude carbamate as an oil: 89.7 g. To a solution of the thus prepared carbamate (45 g) in 90% aqueous acetic acid (575 ml) Zn (84 g) was added in small portions at 30–40° C. After stirring for 3 h excess Zn and Zn salts were filtered off. Water (2 L) was added and extraction with diethyl ether (2×200 ml) removed neutral products. The ice cooled H$_2$O phase was made alkaline (pH>10) by cautiously adding NaOH. Extraction with dichloromethane (4×150 ml) and subsequent work-up yielded 14 g of the title compound 12a as an oil. The fumarate salt crystallized from ethanol. Mp: 176–178° C.

EXAMPLE 13

6-Acetylamino-1-[N-(4-cyclohexylbutan-1-yl)-N-methylaminomethyl]indan, sesquioxalate 13a
(method d)

A mixture of 6-Acetylamino-1-(N-methylaminomethyl) indan (1.5 g), 4-cyclohexylbutan-1-ol mesylate (2.5 g), potassium carbonate (1.4 g), and a crystal of potassium iodide in MIBK (80 ml) were refluxed for 5 h. After cooling inorganic salts were filtered off and the solvent evaporated in vacuo. The remaining oil was subjected to column chromatography on SiO$_2$ (eluted with ethyl acetate: heptane: triethylamine 80:20:4). The free base of the title compound was isolated as an oil. The sesquioxalate of 13a crystallized from acetone. Yield 1.6 g Mp: 145–155° C.

In a corresponding way was prepared the following N,N-disubstituted derivatives:
6-Acetylamino-1-[N-methyl-N-(4-phenylbutan-1-yl) aminomethyl]indan sesquioxalate 13b. Mp: 121–123° C.
6-Acetylamino-1-[N-[4-(indol-3-yl)butan-1-yl]-N-methylaminomethyl]indan, oxalate 13c Mp: 111–113° C.

6-Acetylamino-1-[N-[2-(2-imidazolidinon-1-yl)ethyl]-N-methylaminomethyl]indan, sesquioxalate 13d. Mp: 154–158° C.

6-Acetylamino-1-[N-[2-[3-(4-fluorophenyl)-2-imidazolidinon-1-yl]ethyl]-N-methylaminomethyl]indan, sesquioxalate 13e. Mp: 109–114° C.

6-Acetylamino-1-[N-[4-(3-cyclohexyl-2-imidazolidinon-1-yl)-1-butyl]-N-methylaminomethyl]indan, sesquioxalate 13f. Mp: 98–101° C.

6-Acetylamino-1-[N-methyl-N-[3-(3-phenyl-2-imidazolidinon-1-yl)-1-propyl]aminomethyl]indan, oxalate 13g. Mp: 191–194° C.

6-Acetylamino-1-[N-[4-[3-(4-fluorophenyl)-2-imidazolidinon-1-yl]-1-butyl]-N-methylaminomethyl]indan, oxalate 13h. Mp: 102–106° C.

6-Acetylamino-1-[N-[3-(3-cyclohexyl-2-imidazolidinon-1-yl)-1-propyl]-N-methylaminomethyl]indan, sesquioxalate, hemihydrate 13i. Mp: 108–115° C.

6-Acetylamino-1-[N-[6-(3-cyclopentyl-2-imidazolidinon-1-yl)-1-hexyl]-N-methylaminomethyl]indan, sesquioxalate, hemihydrate 13j. Mp: 87–93° C.

6-Acetylamino-1-[N-[4-(2-imidazolidinon-1-yl)-1-butyl]-N-methylaminomethyl]indan, hemifumarate 13k. Amorphous freeze dried powder.

6-Acetylamino-1-[N-[2-(3-(2-propyl)-2-imidazolidinon-1-yl)ethyl]-N-methylaminomethyl]indan, sesquioxalate, 13l. Mp: 151–154° C.

EXAMPLE 14

6-(N-acetyl-N-ethylamino)-1-(N,N-dipropylaminomethyl)indan, oxalate 14a (method a)

A solution of the free base of compound 2a (5.0 g) in dry THF (25 ml) was added dropwise to a suspension of 1 g LiAlH$_4$ in dry 50 ml THF at 20–25° C. The mixture was refluxed for 2 hours, excess LiAlH$_4$ was destroyed by cautiously adding 2 ml diluted aqueous NaOH solution. Inorganic salts were filtered off and the crude 6-ethylamino-1-(N,N-dipropylaminomethyl(indan was isolated as a viscous oil upon evaportion of the solvents. Yield: 3.0 g. All off the thus obtained ethylaminoindan derivative was dissolved in 60 ml dichloromethane and 2.3 ml triethylamine was added. The mixture was cooled to 0° C. and a solution of 1 ml acetylchloride in 10 ml dichloromethane was added dropwise at 5–10° C. The mixture was stirred for another hour at room temperature. Water (100 ml) was added and the organic phase was subsequently separated and worked up. The remaining oil was dissolved in acetone and oxalic acid was added. The oxalate salt of the title compound 14a crystallized and was filtered off and dried in vacuo. Yield: 2.5 g. Mp: 129–130° C.

The following compound was prepared in a corresponding way using compound 1a as starting material:

6-(N-acetyl-N-methylamino)-1-(N,N-dipropylaminomethyl)indan, oxalate 14b, Mp: 126–129° C.

PHARMACOLOGY

The compounds of Formula I have been tested according to established and reliable pharmacological methods for determination of the affinity to the 5-HT$_{1A}$ receptor and for determination of the in vivo agonistic effects of the compounds with respect to said receptor. The tests were as follows:

Inhibition of $^3$H-8-OH-DPAT Binding to Serotonin 5-HT$_{1A}$ Receptors in Rat Brain in vitro.

By this method the inhibition by drugs of the binding of the 5-HT$_{1A}$ agonist $^3$H-8-OH-DPAT (1 nM) to 5-HT$_{1A}$ receptors in membranes from rat brain minus cerebellum is determined in vitro. Accordingly, this is a test for affinity for the 5-HT$_{1A}$ receptor.

PROCEDURE

Male Wistar (Mol:Wist) rats (125–250 g) are sacrificed and the brain is dissected and weighed. The brain tissue minus cerebellum is homogerized (Ultra Turrax, 20 sec) in 10 ml of ice cold 50 nM Tris buffer pH 8.0 (at 25° C.) containing 120 mM NaCl, 4 mM CaCl$_2$ and 4 mM MgCl$_2$. The homogenate is centrifuged at 20,000 g for 10 min at 4° C. The pellet is homogenized in 10 ml of buffer and incubated at 37° C. for 10 min. The homogenmate is centrifuged as above and the pellet is homogenized in 100 vol (w/v) ice cold buffer containing 10 μM of pargyline.

Incubation tubes kept on ice in triplicate receive 100 μl of drug solution in water (or water for total binding) and 1000 μl of tissue suspension (final tissue content corresponds to 10 mg original tissue). The binding experiment is initiated by addition of 100 μl of $^3$H-8-OH-DPAT (final concentration 1 nM) and by placing the tubes in a 37° C. water bath. After incubation for 15 min the samples are filtered under vacuum (0–50 mBar) through Whatman GF/F filters (25 mm). The tubes are rinsed with 5 ml ice cold 0.9% NaCl which is then poured on the filters. Thereafter, the filters are washed with 2×5 ml 0.9% NaCl. The filters are placed in counting vials and 4 ml of appropriate scintillation fluid (e.g. Picofluor™15) are added. After shaking for 1 h and storage 2 h in the ark the content of radioactivity is determined by liquid scintillation counting. Specific binding is obtained by subtracting the nonspecific binding in the presence of 10 μM of 5-HT.

For determination of the inhibition of binding five concentrations of drugs covering 3 decades are used.

The measured cpm are plotted against drug concentration on semilogarithmic paper, and the best fitting s-shaped curve is drawn. The IC$_{50}$-value is determined as the concentration, at which the binding is 50% of the total binding in control samples minus the nonspecific binding in the presence of 10 μM of 5-HT.

$^3$H-8-OH-DPAT was obtained from Amersham International plc., England. Specific activity approximately 200 Ci/mmol.

8-OH DPAT Cue Agonisme is Rats

This test model is used to determine the agonist effects of a test compound on 5-HT$_{1A}$ receptors in vivo. A related method is described by Tricklebank, M. D., et al, *Eur. J. Pharmacol.*, 1987, 133, 47–56; Arnt, J. *Pharmacology & Toxicology*, 1989, 64, 165.

PROCEDURE

Male Wistar rats are trained to discriminate between 8-OH-DPAT (0.4 mg/kg, i.p., 15 min pretreatment) and physiological saline in operant chambers equipped with two response levers. Between the levers a dipper is placed, where water rewards (0.1 ml) are presented. The rats are water deprived for at least 24 h and work in a fixed ratio (FR) schedule (final FT=32).

Following 8-OH-DPAT administration responding is reinforced only on a designated (drug) lever, whereas responding on the opposite lever has no consequences. Following saline administration responding is reinforced on the lever opposite to the drug lever. Drug and saline trials alternate randomly between days. The level of discrimination occuracy is expressed as the per cent drug responses and is calculated as the number of correct responses ×100 divided by the sum of the correct and incorrect responses before the first reward. The time to the first reward is also recorded as a measure of reaction time. When stable occuracy (means correst responding=90%, individual rats at least 75% correct responding) is obtained test sessions are included between training days. Test compound is injected s.c. usually 30 min or 45 min, respectively, before beginning of the test. The test trial is terminated when a total of 32 responses are made on either lever or when 20 min have elapsed. No reward is given and the rats have free access to water for 20–30 min after the test. The effects are expressed as per cent drug responding. Only results from rats making at least 10 responses on one lever are included in data analysis. Furthermore, only test sessions in which at least half of the rats respond are included.

The per cent inhibition of drug response obtained for each dose of test compound is used to calculate $ED_{50}$ values by log-probit analysis.

The results obtained will appear from the following Table 1;

The known $5\text{-}HT_{1A}$ receptor ligands 8-OH DPAT and buspirone were included in the tests for comparison purposes.

TABLE 1

Pharmacological Test Data

| Compound No. | $^3$H 8-OH DPAT binding $IC_{50}$ nM | 8-OH DPAT Cue Agonism $ED_{50}$ μM/kg |
|---|---|---|
| 1a | 4.1 | 0.0052 |
| 1b | 110. | 0.41 |
| 1c | 42. | 0.33 |
| 1d | 19. | |
| 2a | 0.89 | 0.010 |
| 2b | 25. | 0.21 |
| 2c | 5.1 | 2.2 |
| 2f | 340. | |
| 2g | 16. | 0.93 |
| 2h | 2000. | |
| 2i | 6.3 | |
| 3a | 0.56 | |
| 4a | 80. | |
| 4b | 6.6 | |
| 4c | 10. | 0.42 |
| 4d | 170. | |
| 4e | 170. | |
| 5a | 3.4 | 0.046 |
| 5b | 60. | |
| 5c | 6.5 | |
| 6a | 20. | |
| 8a | 0.64 | 0.0089 |
| 8b | 0.64 | 0.031 |
| 8e | 6.7 | 0.043 |
| 8f | 15. | 0.15 |
| 10a | 1.0 | 0.010 |
| 10b | 4.2 | 0.058 |
| 10c | 8.1 | |
| 10d | 22. | |
| 10e | 160. | |
| 10f | 63. | |
| 10g | 48. | 0.12 |
| 10h | 220. | 1.9 |
| 11a | 21. | 0.26 |
| 11b | 15. | 0.44 |
| 11c | 14. | 0.38 |
| 11d | 120 | |
| 12a | 25. | |
| 13a | 1.4 | 0.15 |

TABLE 1-continued

Pharmacological Test Data

| Compound No. | $^3$H 8-OH DPAT binding $IC_{50}$ nM | 8-OH DPAT Cue Agonism $ED_{50}$ μM/kg |
|---|---|---|
| 13b | 3.4 | 0.22 |
| 13c | 1.5 | 0.66 |
| 13d | 1.8 | 0.61 |
| 13e | 27. | |
| 13f | 5.1 | |
| 13g | 1.0 | |
| 13h | 4.8 | |
| 13i | 2.2 | |
| 13j | 3.2 | |
| 13k | 790. | |
| 8-OH DPAT | 3.5 | 0.10 |
| buspirone | 41 | 0.62 |

It appears from the above tables that the compounds of the invention are $5\text{-}HT_{1A}$ receptor ligands inhibiting the binding of tritiated 8-hydroxy-2-dipropylaminotetralin (8-OH-DPAT) to $5\text{-}HT_{1A}$ receptors in vitro, many of them with potencies better than 50 nM, and even in the range from about 0.5 to 10 nM. It is also seen that in general they have potent $5\text{-}HT_{1A}$ agonistic properties in vivo.

Furthermore, the compounds of the invention were tested with respect to affinity for the dopamine $D_2$ receptor by determining their ability to inhibit the binding of $^3$H-spiroperidol to $D_2$ receptors by the method of Hyttel et al, *J. Neurochem.*, 1985, 44, 1615.

The compounds were also tested in the Methylphenidate test as published by Pedersen and Christensen in Acta Pharmacol. et Toxical. 31, 488–496 (1972).

In a further test, evaluation of catalepsy was made according to the method of Sanchez, C. et al.; *Drug Dev. Res.* 1991, 22, 239–250.

The compounds of the invention tested were found to be substantially without affinity to dopamine $D_2$ receptors and to be without any cataleptogenic effects in the highest dose tested, whereas many of them showed effect in the Methylphenidate Test with $ED_{50}$ values in the μmol/kg range. These test results indicate that the compounds of the invention have antipsychotic properties without showing extrapyramidal side effects.

Finally, the compounds of the invention were tested with respect to anxiolytic properties by measuring their ability to inhibit foot shock-induced ultrasonic vocalisation. Adult rats emit ultrasonic distress calls as response to unavoidable aversive stimuli such as foot shock. This has been suggested as a test model of anxiety (Tonoue T. et al., *Psychoneuroendocrinology*, 1986, 11, No. 2, 177–184).

The compounds tested showed potent anxiolytic effects in this test with $ED_{50}$ values generally in the range from 0.03 to 1.0 μmol/kg.

FORMULATION EXAMPLES

The pharmaceutical formulations of the invention may be prepared by conventional methods in the art.

For example: Tablest may be prepared by mixing the active ingredient with ordinary adjuvants and/or diluents and subsequently compressing the mixture in a conventional tabletting machine. Examples of adjuvants or diluents comprise: corn strach, potato starch, talcum, magnesium stearate, gelatine, lactose, gums, and the like. Any other adjuvants or additives usually used for such purposes such as colurings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilization of the solution and filling suitable ampules or vials. Any suitable additive conventionally used in the art may be added, such as tonicity agents, preservatives, antioxidants, etc.

Typical examples of recipes for the formulation of the invention are as follows:

| 1) Tablets containing 5.0 mg of Compound 1 calculated as the free base: | |
|---|---|
| Compound 1a | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |
| 2) Tablets containing 0.5 mg of Compound 2b calculated as the free base: | |
| Compound 2b | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |
| 3) Syrup containing per milliliter: | |
| Compound 1c | 2.5 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 ml |
| Flavour | 0.05 mg |
| Saccharin natrium | 0.5 mg |
| Water | ad 1 ml |
| 4) Solution for injection containing per milliliter: | |
| Compound 10j | 0.5 mg |
| Sorbitol | 5.1 mg |
| Acetic acid | 0.08 mg |
| Water for injection | ad 1 ml |

I claim:

1. A compound having Formula I:

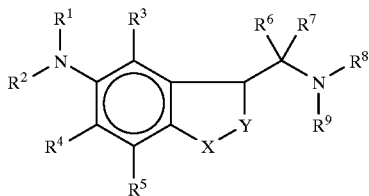

I wherein one of X and Y is $CH_2$ and the other one is selected from the group consisting of $CH_2$, O and S;

$R^1$ is selected from the group consisting of lower alkyl, lower alkenyl, lower alkynyl, cycloalk(en)yl, cycloalk(en)yl-lower alk(en/yn)yl, aryl-lower alkyl, acyl, lower-alkyl sulphonyl, trifluoromethylsulfonyl, arylsulphonyl, and $R^{10}ZCO$— where Z is O or S and $R^{10}$ is alkyl, alkenyl, alkynyl, cycloalk(en)yl, cycloalk(en)ylalkyl, or aryl, or $R^{11}R^{12}NCO$— where $R^{11}$ and $R^{12}$ are independently hydrogen, alkyl, alkenyl, alkynyl, cycloalk(en)yl, cycloalk(en)ylalk(en/yn)yl, or aryl;

$R^2$ is selected from the group consisting of hydrogen, lower alkyl, lower alkenyl, lower alkynyl, cycloalk(en)yl, cycloalk(en)yl-lower alk(en/yn)yl, and aryl-lower alkyl $R^3-R^5$ are independently selected from the group consisting of hydrogen, halogen, lower alkyl, lower alkoxy, acyl, lower alkylthio, hydroxy, lower alkylsulphonyl, cyano, trifluoromethyl, cycloalkyl, cycloalkylalkyl or nitro;

$R^6$ and $R^7$ are each hydrogen or lower alkyl or they are linked together to constitute a 3–7-membered carbocyclic ring;

$R^8$ and $R^9$ are linked together in order to form a 3–7 membered ring containing one nitrogen atom;

any alkyl, cycloalkyl or cycloalkylalkyl group present being optionally substituted with one or two hydroxy groups, which are optionally esterified with an aliphatic or aromatic carboxylic acid; and any aryl substituent present being optionally substituted with halogen, lower alkyl, lower alkoxy, lower alkylthio, hydroxy, lower alkylsulfonyl, cyano, trifluoromethyl, cycloalkyl, cycloalkylalkyl or nitro; and pharmaceutically acceptable acid addition salts thereof.

2. A compound of claim 1, wherein X is $CH_2$, O or S and Y is $CH_2$.

3. A compound of claim 1, wherein $R^1$ is an aryl-lower alkyl group, an acyl group, a lower alkylsulfonyl group or a group $R^{11}R^{12}N$—CO—, wherein $R^{11}$ is hydrogen or lower alkyl and $R^{12}$ is hydrogen, alkyl, aryl, or cycloalkyl and $R^2$ is hydrogen or lower alkyl.

4. A compound of claim 3, wherein $R^1$ is benzyl or substituted benzyl, formyl, alkylcarbonyl, arylcarbonyl, or a group $R^{11}R^{12}N$—CO—, wherein $R^{11}$ is hydrogen or lower alkyl and $R^{12}$ is hydrogen, lower alkyl, phenyl, substituted phenyl, or $C_{5-6}$ cycloalkyl.

5. A compound of claim 1, wherein $R^3$, $R^4$, and $R^5$ are hydrogen or halogen, and $R^6$ and $R^7$ are both hydrogen.

6. A pharmaceutical composition comprising at least one compound of claim 1 or a pharmaceutically acceptable acid addition salt thereof in a therapeutically effective amount and in combination with one or more pharmaceutically acceptable carriers or diluents.

7. A method for treating psychosis, anxiety disorders, depression, impulse control disorders, alcohol abuse, aggression, ischemic diseases, side effects induced by conventional antipsychotic agents or cardiovascular disorders in humans comprising administering in an effective amount to said humans a compoung having the formula:

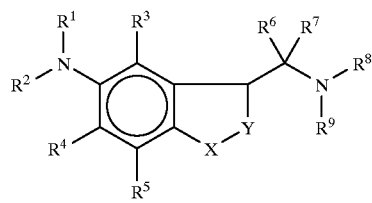

I wherein one of X and Y is $CH_2$ and the other one is selected from the group consisting of $CH_2$, O, and S;

$R^1$ is selected from the group consisting of lower alkyl, lower alkenyl, lower alkynyl, cycloalk(en)yl, cycloalk(en)yl-lower alk(en/yn)yl, aryl-lower alkyl, acyl, lower-alkyl sulfonyl, trifluoromethylsulfonyl arylsulfonyl, and $R^{10}ZCO$-where Z is O or S and $R^{10}$ is alkyl, alkenyl, alkynyl, cycloalk(en)ylalkyl, or aryl, or $R^{11}R^{12}NCO$-wherein $R^{11}$ and $R^{12}$ are independently hydrogen, alkyl, alkenyl, alkynyl, cycloalk(en)yl, cycloalk(en)yl alk(en/yn)yl, or aryl;

$R^2$ is selected from the group consisting of hydrogen, lower alkyl, lower alkenyl, lower alkynyl, cycloalk(en)yl, cycloalkenyl-lower alk(en/yn)yl, cycloalkenyl-lower alk(en/yn)yl, aryl-lower alkyl;

$R^3$–$R^5$ are independently selected from the group consisting of hydrogen, halogen, lower alkyl, lower alkoxy, acyl, lower alkylthio, hydroxy, lower alkylsulfonyl, cyano, trifluoromethyl, cycloalkyl, cycloalkylalkyl and nitro;

$R^6$ and $R^7$ are each hydrogen or lower alkyl or they are linked together to constitute a 3–7-membered carbocyclic ring;

$R^8$ and $R^9$ are linked together in order to form a 3–7 membered ring containing one nitrogen atom;

any alkyl, cycloalkyl or cycloalkylalkyl group present being optionally substituted with one or two hydroxy groups, which are optionally esterified with an aliphatic or aromatic carboxylic acid; and any aryl substituent present being optionally substituted with halogen, lower alkyl, lower alkoxy, lower alkythio, hydroxy, lower alkylsufonyl, cyano, trifluoromethyl, cycloalkyl, cycloalkylalkyl or nitro; and pharmaceutically acceptable acid addition salts thereof.

8. A compound having formula I:

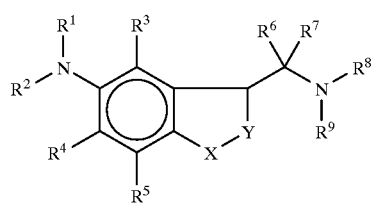

I wherein one of X and Y is $CH_2$ and the other one is selected from the group consisting of $CH_2$, O and S;

$R^1$ is selected from the group consisting of lower alkyl, lower alkenyl, lower alkynyl, cycloalk(en)yl, cycloalk(en)yl-lower alk(en/yn)yl, aryl-lower alkyl, acyl, lower-alkyl sulphonyl, trifluoromethylsulfonyl, arylsulphonyl, and $R^{10}ZCO$— where Z is O or S and $R^{10}$ is alkyl, alkenyl, alkynyl, cycloalk(en)yl, cycloalk(en)ylalkyl, or aryl, or $R^{11}R^{12}NCO$— where $R^{11}$ and $R^{12}$ are independently hydrogen, alkyl, alkenyl, alkynyl, cycloalk(en)yl, cycloalk(en)ylalk(en/yn)yl, or aryl;

$R^2$ is selected from the group consisting of hydrogen, lower alkyl, lower alkenyl, lower alkynyl, cycloalk(en)yl, cycloalk(en)yl-lower alk(en/yn)yl, and aryl-lower alkyl;

$R^3$–$R^5$ are independently selected from the group consisting of hydrogen, halogen, lower alkyl, lower alkoxy, acyl, lower alkylthio, hydroxy, lower alkylsulphonyl, cyano, trifluoromethyl, cycloalkyl, cycloalkylalkyl or nitro;

$R^6$ and $R^7$ are each hydrogen or lower alkyl or they are linked together to constitute a 3–7-membered carbocyclic ring;

$R^8$ and $R^9$ are independently hydrogen, alkyl, alkenyl, alkynyl, cycloalk(en)yl, cycloalk(en)yl-alk(en/yn)yl, and arylalkyl;

any alkyl, cycloalkyl or cycloalkylalkyl group present being optionally substituted with one or two hydroxy groups, which are optionally esterified with an aliphatic or aromatic carboxylic acid; and any aryl substituent present being optionally substituted with halogen, lower alkyl, lower alkoxy, lower alkylthio, hydroxy, lower alkylsulfonyl, cyano, trifluoromethyl, cycloalkyl, cycloalkylalkyl or nitro; and pharmaceutically acceptable acid addition salt thereof.

9. A compound of claim 8, wherein X is $CH_2$, O or S and Y is $CH_2$.

10. A compound of claim 8, wherein $R^1$ is an aryl-lower alkyl group, an acyl group, a lower alkylsulfonyl group or a group $R^{11}R^{12}N$—CO—, wherein $R^{11}$ is hydrogen or lower alkyl and $R^{12}$ is hydrogen, alkyl, aryl, or cycloalkyl and $R^2$ is hydrogen or lower alkyl.

11. A compound of claim 10, wherein $R^1$ is benzyl or substituted benzyl, formyl, alkylcarbonyl, arylcarbonyl, or a group $R^{11}R^{12}N$—CO—, wherein $R^{11}$ is hydrogen or lower alkyl and $R^{12}$ is hydrogen, lower alkyl, phenyl, substituted phenyl, or $C_{5-6}$ cycloalkyl.

12. A compound of claim 8, wherein $R^3$, $R^4$, and $R^5$ are hydrogen or halogen, and $R^6$ and $R^7$ are both hydrogen.

13. A pharmaceutical composition comprising at least one compound of claim 8 or a pharmaceutically acceptable acid addition salt thereof in a therapeutically effective amount and in combination with one or more pharmaceutically acceptable carriers or diluents.

14. A method for treating psychosis, anxiety disorders, depression, impulse control disorders, alcohol abuse, aggression, ischemic diseases, side effects induced by conventional antipsychotic agents or cardiovascular disorders in humans comprising administering in an effective amount to said humans a compound having the formula:

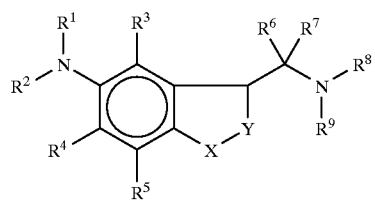

I wherein one of X and Y is $CH_2$ and the other one is selected from the group consisting of $CH_2$, O, and Si;

$R^1$ is selected from the group consisting of lower alkyl, lower alkenyl, lower alkynyl, cycloalk(en)yl, cycloalk(en)yl-lower alk(en/yn)yl, aryl-lower alkyl, acyl, lower-alkyl sulfonyl, trifluoromethylsulfonyl, arylsulfonyl, and $R^{10}ZCO$-where Z is O or S and $R^{10}$ is alkyl, alkenyl, alkynyl, cycloalk(en)ylalkyl, or aryl, or $R^{11}R^{12}NCO$-wherein $R^{11}$ and $R^{12}$ are independently hydrogen, alkyl, alkenyl, alkynyl, cycloalk(en)yl, cycloalk(en)yl alk(en/yn)yl, or aryl;

$R^2$ is selected from the group consisting of hydrogen, lower alkyl, lower alkenyl, lower alkynyl, cycloalk(en)yl, cycloalkenyl-lower alk(en/yn)yl, cycloalkenyl-lower alk(en/yn)yl, aryl-lower alkyl, $R^3$–$R^5$ are independently selected from the group consisting of hydrogen, halogen, lower alkyl, lower alkoxy, acyl, lower alkylthio, hydroxy, lower alkylsulfonyl, cyano, trifluoromethyl, cycloalkyl, cycloalkylalkyl and nitro;

$R^6$ and $R^7$ are each hydrogen or lowr alkyl or they are linked together to constitute a 3–7-membered carbocyclic ring;

$R^8$ and $R^9$ are independently hydrogen, alkyl, alkenyl, alkynyl, cycloalk(en)yl, cycloalk(en)yl-alk(en/yn)yl, and arylalkyl;

any alkyl, cycloalkyl or cycloalkylalkyl group present being optionally substituted with one or two hydroxy groups, which are optionally esterified with an aliphatic or aromatic carboxylic acid; and any aryl substituent present being optionally substituted with halogen, lower alkyl, lower alkoxy, lower alkythio, hydroxy, lower alkysulfonyl, cyano, trifluoromethyl, cycloalkyl, cycloalkylalkyl or nitro; and pharmaceutically acceptable acid addition salts thereof.

* * * * *